US009687170B2

(12) United States Patent
Washburn et al.

(10) Patent No.: US 9,687,170 B2
(45) Date of Patent: Jun. 27, 2017

(54) SYSTEM AND METHOD FOR PERFORMING MAGNETIC RESONANCE IMAGING SCAN OPERATIONS FROM WITHIN A SCAN ROOM

(75) Inventors: Sheila S. Washburn, Brookfield, WI (US); David B. Ferguson, Hartland, WI (US); Michael R. Figueira, Waukesha, WI (US); Thisath C. Kularatna, Gurnee, IL (US); Donna M. Callan, Pewaukee, WI (US)

(73) Assignee: General Electric Company, Schenectady, NY (US)

( * ) Notice: Subject to any disclaimer, the term of this patent is extended or adjusted under 35 U.S.C. 154(b) by 1555 days.

(21) Appl. No.: 12/045,935

(22) Filed: Mar. 11, 2008

(65) Prior Publication Data
US 2009/0234218 A1 Sep. 17, 2009

(51) Int. Cl.
*A61B 5/05* (2006.01)
*A61B 5/055* (2006.01)
*G01R 33/28* (2006.01)
*G01R 33/54* (2006.01)
*A61B 5/00* (2006.01)

(52) U.S. Cl.
CPC ............ *A61B 5/055* (2013.01); *G01R 33/283* (2013.01); *G01R 33/543* (2013.01); *A61B 5/0046* (2013.01)

(58) Field of Classification Search
USPC ....... 600/407, 410, 411, 413, 414, 415, 422, 600/424–428
See application file for complete search history.

(56) References Cited

U.S. PATENT DOCUMENTS

| | | | |
|---|---|---|---|
| 5,184,074 A | 2/1993 | Arakawa et al. | |
| 5,365,927 A | 11/1994 | Roemer et al. | |
| 5,432,544 A | 7/1995 | Ziarati | |
| 5,526,812 A | 6/1996 | Dumoulin et al. | |
| 5,638,001 A | 6/1997 | Vrijheid et al. | |
| 5,694,142 A | 12/1997 | Dumoulin et al. | |
| 5,978,697 A | 11/1999 | Maytal et al. | |
| 6,198,285 B1 | 3/2001 | Kormos et al. | |
| 6,275,721 B1 | 8/2001 | Darrow et al. | |
| 6,400,155 B2 * | 6/2002 | Kormos | A61B 5/0017 324/318 |
| 6,557,558 B1 * | 5/2003 | Tajima et al. | 128/897 |
| 6,731,880 B2 * | 5/2004 | Westbrook et al. | 398/115 |
| 8,423,119 B2 * | 4/2013 | Krueger et al. | 600/414 |
| 2001/0035752 A1 * | 11/2001 | Kormos et al. | 324/307 |

(Continued)

FOREIGN PATENT DOCUMENTS

WO    WO 98/32388    7/1998

*Primary Examiner* — Long V Le
*Assistant Examiner* — Bradley Impink

(57) ABSTRACT

A magnetic resonance imaging (MRI) system includes an imaging assembly located in a scan room and a controller coupled to the imaging assembly and located in a separate control room. A display is coupled to the controller and located in the scan room. The display is configured to display at least one graphical user interface relating to the set up of a patient and a scan for a magnetic resonance imaging (MRI) exam. An input device is also located in the scan room and is coupled to the display and the controller. The input device is configured to receive data regarding the set up of a patient and a scan for the MRI exam.

24 Claims, 6 Drawing Sheets

(56) References Cited

U.S. PATENT DOCUMENTS

| | | | |
|---|---|---|---|
| 2002/0198997 A1* | 12/2002 | Linthicum | H04L 69/329 709/227 |
| 2005/0201510 A1* | 9/2005 | Mostafavi | 378/8 |
| 2006/0026035 A1* | 2/2006 | Younkes et al. | 705/2 |
| 2006/0152220 A1* | 7/2006 | Nabetani et al. | 324/309 |
| 2008/0027306 A1* | 1/2008 | Washburn et al. | 600/410 |
| 2009/0154783 A1* | 6/2009 | Bystrov et al. | 382/131 |

* cited by examiner

SYSTEM AND METHOD FOR PERFORMING MAGNETIC RESONANCE IMAGING SCAN OPERATIONS FROM WITHIN A SCAN ROOM

FIELD OF THE INVENTION

The present invention relates generally to magnetic resonance imaging (MRI) systems and in particular, to a system and methods for performing magnetic resonance imaging (MRI) scan operations from within a scan room.

BACKGROUND OF THE INVENTION

Magnetic resonance imaging (MRI) systems are useful for producing images of, for example, a wide range of soft tissues. MRI scanners typically use a computer to create images based on the operation of a magnet, a gradient coil assembly, and a radio frequency coil(s). The magnet creates a uniform main magnetic field that makes nuclei responsive to radio frequency excitation. The gradient coil assembly imposes a series of pulsed, spatial-gradient magnetic fields upon the main magnetic field to give each point in the volume a spatial identity corresponding to its unique set of magnetic fields during the imaging pulse sequence. The radio frequency coil creates an excitation frequency pulse that temporarily creates an oscillating transverse magnetization that is detected by the radio frequency coil and used by the computer to create the image. An image may be created using one of many known reconstruction techniques.

Various portions of an MRI system, such as an imaging assembly and an operator console, may be located in separate rooms, such as a scan room and a control room, respectively. For example, typically, the imaging assembly (including the magnet, gradient coil assembly, radio frequency coil, etc.) and patient table are enclosed in a scan room. A computer system and an operator console are located in a control room adjacent to the scan room. For an MRI scan, typically an operator or technologist utilizes the operator console to, for example, enter patient information, enter scan parameters and load any scanning protocols. Then the technologist enters the scan room to set up the patient on the patient table. Once the patient is set up, the technologist then returns back to the operator console in the adjacent room to complete patient and scan set-up (e.g., coil selection, etc.) and to manually start the MRI scan.

It would be advantageous to provide a system and method to improve the efficiency, workflow and throughput of an MRI scan. In particular, it would be desirable to provide a system and methods for performing MRI scan operations from within the scan room.

BRIEF DESCRIPTION OF THE INVENTION

In accordance with an embodiment, a method for configuring a magnetic resonance imaging (MRI) exam includes receiving information regarding set up of a patient and a scan for the MRI exam using a display and an input device in a scan room of a magnetic resonance imaging system and displaying a set of patient and scan data on the display in the scan room based on the received information.

In accordance with another embodiment, a magnetic resonance imaging (MRI) system includes an imaging assembly located in a scan room, a controller coupled to the imaging assembly and located in a separate control room, a display coupled to the controller and located in the scan room, the display configured to display at least one graphical user interface relating to the set up of a patient and a scan for a magnetic resonance imaging (MRI) exam and an input device coupled to the display and the controller, the input device located in the scan room and configured to receive data regarding the set up of a patient and a scan for the MRI exam.

In accordance with another embodiment, a method for operating a magnetic resonance imaging (MRI) system includes receiving a request for a set of operator instructions regarding a function of the MRI system, the request received using a display and an input device in a scan room of the MRI system and displaying the set of operator instructions on the display in the scan room.

DESCRIPTION OF THE DRAWINGS

The invention will become more fully understood from the following detailed description, taken in conjunction with the accompanying drawings, in which.

DETAILED DESCRIPTION

Figure 1:
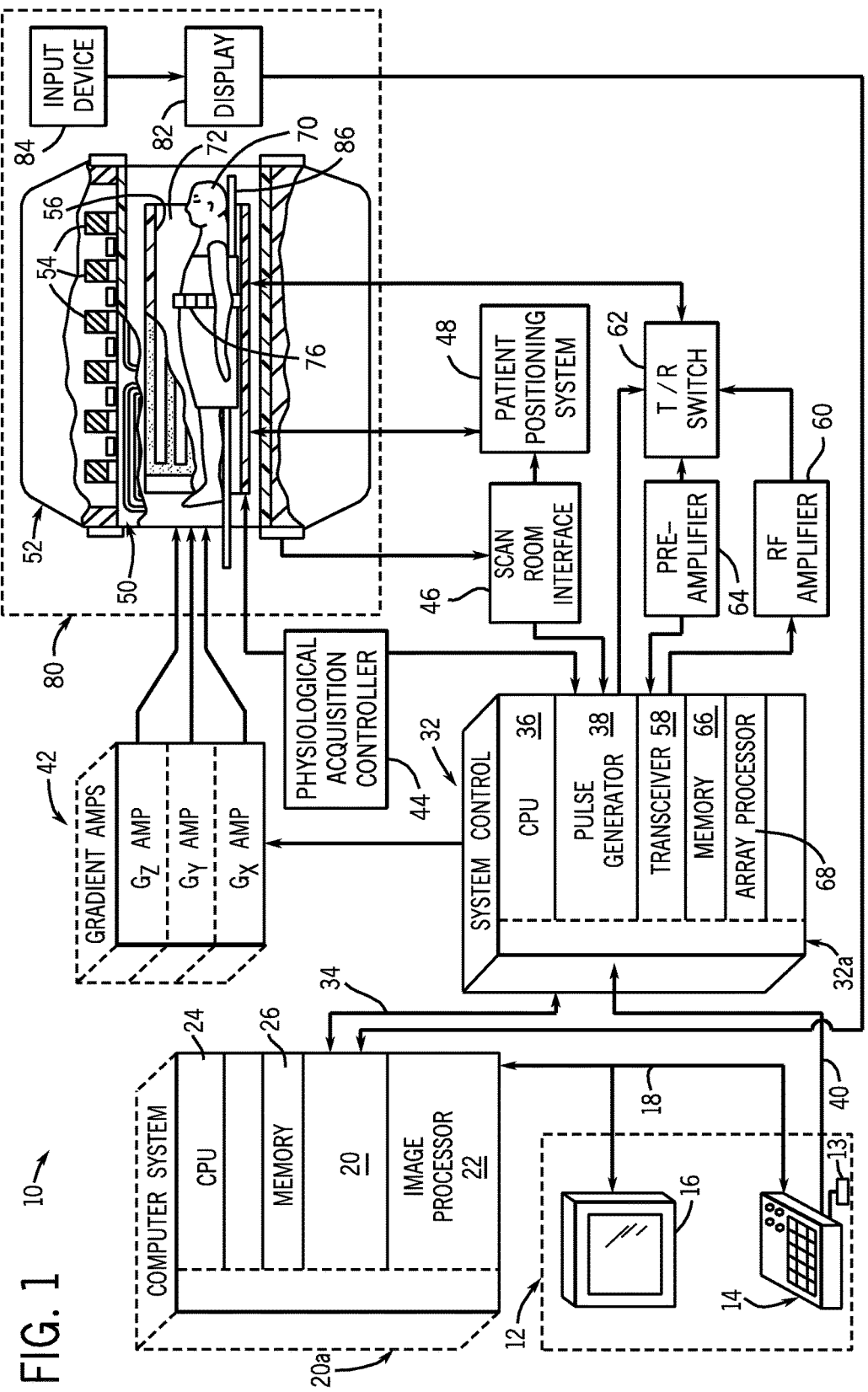
FIG. 1 is a schematic block diagram of a magnetic resonance imaging system in accordance with an embodiment.

FIG. 1 is a schematic block diagram of a magnetic resonance imaging system in accordance with an embodiment. The operation of MRI system 10 may be controlled from an operator console 12 that includes a keyboard or other input device 13, a control panel 14, and a display 16. The operator console 12 is located in a room (e.g., a control room) that is separate from a scan room 80. A patient table 86 and an imaging assembly 52 are located in the scan room 80. Accordingly, the scan room 80 separates a patient or subject 70, the patient table 86 and imaging assembly 52 from the equipment (e.g., the operator console 12, a computer system 20, a system control 32, gradient amplifiers 42, etc.) located in the adjacent control room. Typically, scan room 80 is shielded to provide shielding for RF and magnetic signals generated by the equipment in the control room and the scan room 80. A display 82 and/or an input device 84 are located in the scan room 80 and are configured to view and control various operations of the MRI system 10 as described further below with respect to FIGS. 2-6. Display 82 may be, for example, a computer screen, a liquid crystal display (LCD), a projector screen, etc. that is compatible with the environment in the MRI scan room 80. The input device 84 in the scan room 80 may include a mouse, joystick, keyboard, track ball, touch activated screen (e.g., the screen of display 82), light wand, voice control or any similar or equivalent input device that is compatible with the environment in the MRI scan room 80. For example, display 82 and input device 84 may be constructed with materials compatible with the scan room environment or may be shielded (e.g., RF shielding) within the scan room 80, as is known in the art. Display 82 and/or input device 84 are coupled to a computer system 20 in the control room by, for example, a cable, to communicate signals and information (e.g., control signals, video signals) between the computer system 20 and the display 82 and input device 84. For example, fiber optic cables or shielded coaxial cables may be used to permit the transmission of signals without leaking RF signals that can cause RF noise in the scan room 80.

The operator console 12 communicates through a link 18 with a computer system 20 and provides an interface for an operator to prescribe MRI scans, display resultant images, perform image processing on the images, and archive data and images. The computer system 20 includes a number of modules that communicate with each other through electrical and/or data connections, for example, such as are provided by using a backplane 20a. Data connections may be direct-wired links or may be fiber optic connections or wireless communication links or the like. The modules of the computer system 20 include an image processor module 22, a CPU module 24 and a memory module 26 that may include a frame buffer for storing image data arrays. In an alternative embodiment, the image processor module 22 may be replaced by image processing functionality on the CPU module 24. The computer system 20 is linked to archival media devices, permanent or back-up memory storage or a network. Computer system 20 may also communicate with a separate system control computer 32 through a link 34. The input device 13 can include a mouse, joystick, keyboard, track ball, touch activated screen, light wand, voice control, or any similar or equivalent input device, and may be used for interactive geometry prescription.

The system control computer 32 includes a set of modules in communication with each other via electrical and/or data connections 32a. Data connections 32a may be direct wired links, or may be fiber optic connections or wireless communication links or the like. In alternative embodiments, the modules of computer system 20 and system control computer 32 may be implemented on the same computer system or a plurality of computer systems. The modules of system control computer 32 include a CPU module 36 and a pulse generator module 38 that connects to the operator console 12 through a communications link 40. The pulse generator module 38 may alternatively be integrated into the scanner equipment (e.g., imaging assembly 52). It is through link 40 that the system control computer 32 receives commands from the operator to indicate the scan sequence that is to be performed. The pulse generator module 38 operates the system components that play out (i.e., perform) the desired pulse sequence by sending instructions, commands and/or requests (e.g., radio frequency (RF) waveforms) describing the timing, strength and shape of the RF pulses and pulse sequences to be produced and the timing and length of the data acquisition window. The pulse generator module 38 connects to a gradient amplifier system 42 and produces data called gradient waveforms which control the timing and shape of the gradient pulses that are to be used during the scan. The pulse generator module 38 may also receive patient data from a physiological acquisition controller 44 that receives signals from a number of different sensors connected to the patient, such as ECG signals from electrodes attached to the patient. The pulse generator module 38 connects to a scan room interface circuit 46 that receives signals from various sensors associated with the condition of the patient and the magnet system. It is also through the scan room interface circuit 46 that a patient positioning system 48 receives commands to move the patient table to the desired position for the scan.

The gradient waveforms produced by the pulse generator module 38 are applied to gradient amplifier system 42 which is comprised of $G_x$, $G_y$ and $G_z$ amplifiers. Each gradient amplifier excites a corresponding physical gradient coil in a gradient coil assembly generally designated 50 to produce the magnetic field gradient pulses used for spatially encoding acquired signals. The gradient coil assembly 50 forms part of an imaging assembly 52 that includes a polarizing superconducting magnet with superconducting main coils 54. Imaging assembly 52 may include a whole-body RF coil 56, surface or parallel imaging coils 76 or both. The coils 56, 76 of the RF coil assembly may be configured for both transmitting and receiving or for transmit-only or receive-only. A patient or imaging subject 70 may be positioned within a cylindrical patient imaging volume 72 of the imaging assembly 52. A transceiver module 58 in the system control computer 32 produces pulses that are amplified by an RF amplifier 60 and coupled to the RF coils 56, 76 by a transmit/receive switch 62. The resulting signals emitted by the excited nuclei in the patient may be sensed by the same RF coil 56 and coupled through the transmit/receive switch 62 to a preamplifier 64. Alternatively, the signals emitted by the excited nuclei may be sensed by separate receive coils such as parallel coils or surface coils 76. The amplified MR signals are demodulated, filtered and digitized in the receiver section of the transceiver 58. The transmit/receive switch 62 is controlled by a signal from the pulse generator module 38 to electrically connect the RF amplifier 60 to the RF coil 56 during the transmit mode and to connect the preamplifier 64 to the RF coil 56 during the receive mode. The transmit/receive switch 62 can also enable a separate RF coil (for example, a parallel or surface coil 76) to be used in either the transmit or receive mode.

The MR signals sensed by the RF coil 56 are digitized by the transceiver module 58 and transferred to a memory module 66 in the system control computer 32. Typically, frames of data corresponding to MR signals are stored temporarily in the memory module 66 until they are subsequently transformed to create images. An array processor 68 uses a known transformation method, most commonly a Fourier transform, to create images from the MR signals. These images are communicated through the link 34 to the computer system 20 where it is stored in memory. In response to commands received from the operator console 12, this image data may be archived in long-term storage or it may be further processed by the image processor 22 and conveyed to the operator console 12 and presented on display 16.

Figure 2:
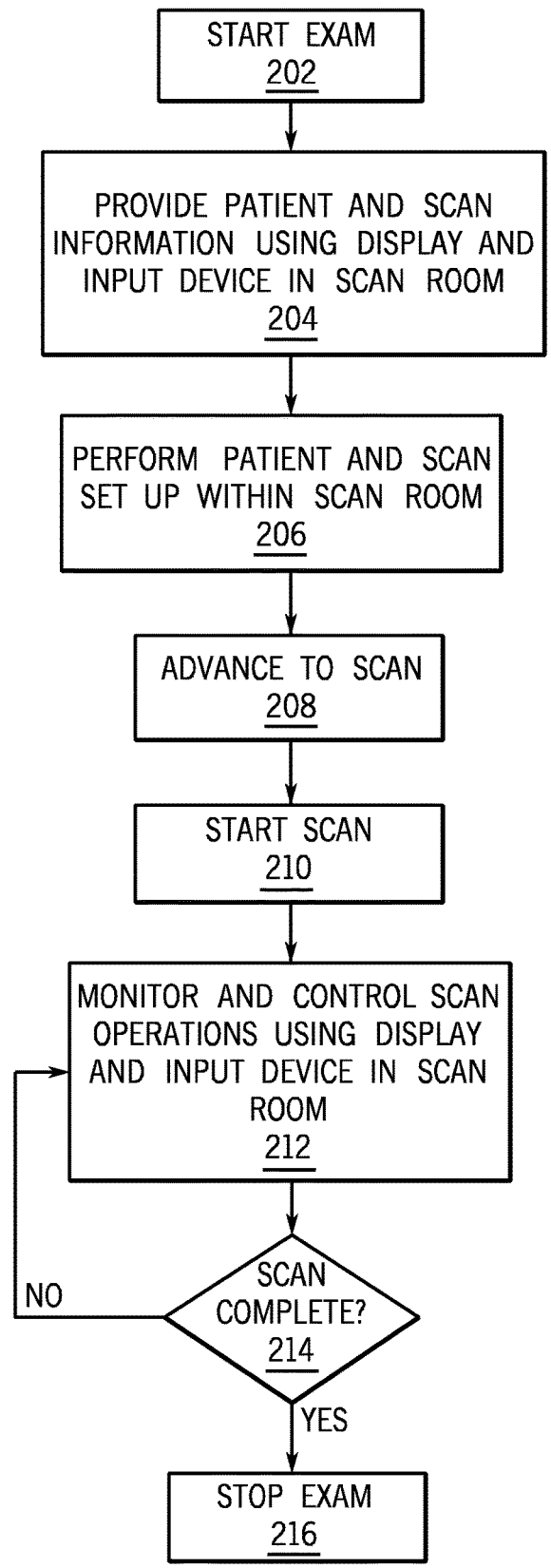
FIG. 2 is a flow chart illustrating a method for performing a magnetic resonance imaging (MRI) exam utilizing a display and input device within a scan room in accordance with an embodiment.

As mentioned above, the display 82 and input device 84 in the scan room 80 are configured to enable an operator or user to perform and control scanner operations and workflow from within the scan room 80. FIG. 2 is a flow chart illustrating a method for performing a magnetic resonance imaging (MRI) exam utilizing a display and input device within a scan room in accordance with an embodiment. At block 202, the operator or user begins an MRI exam. For example, the operator may collect patient information or collect information regarding the procedure. At block 204, the operator provides patient information and scan information using the display 82 (shown in FIG. 1) and input device 84 (shown in FIG. 1) in the scan room 80 (shown in FIG. 1).

Accordingly, the operator does not need to leave the scan room in order to provide the necessary patient and scan information for the MRI exam. Patient information includes, but is not limited to, for example, patient identification information (e.g., a patient ID, name, birth date), gender, weight, height, age, maximum breath-holding time, preferred pulse sequence, a maximum exam time, the name of the referring physician, the name of the radiologist, operator, reference, status, exam description and history. Scan information includes, but is not limited to, for example, scan parameters and a protocol for the MRI exam. Scan parameters include, but are not limited to, for example, field of view (FOV), slice thickness, slices per frame, slice spacing, echo time (TE), repetition time (TR), flip angles for RF pulses, frequency encoding direction, matrix size (i.e., a number of phase encoding steps and frequency encoding steps), refocusing pulse spacing in a fast spin echo (FSE) sequence, etc.

Figure 3:
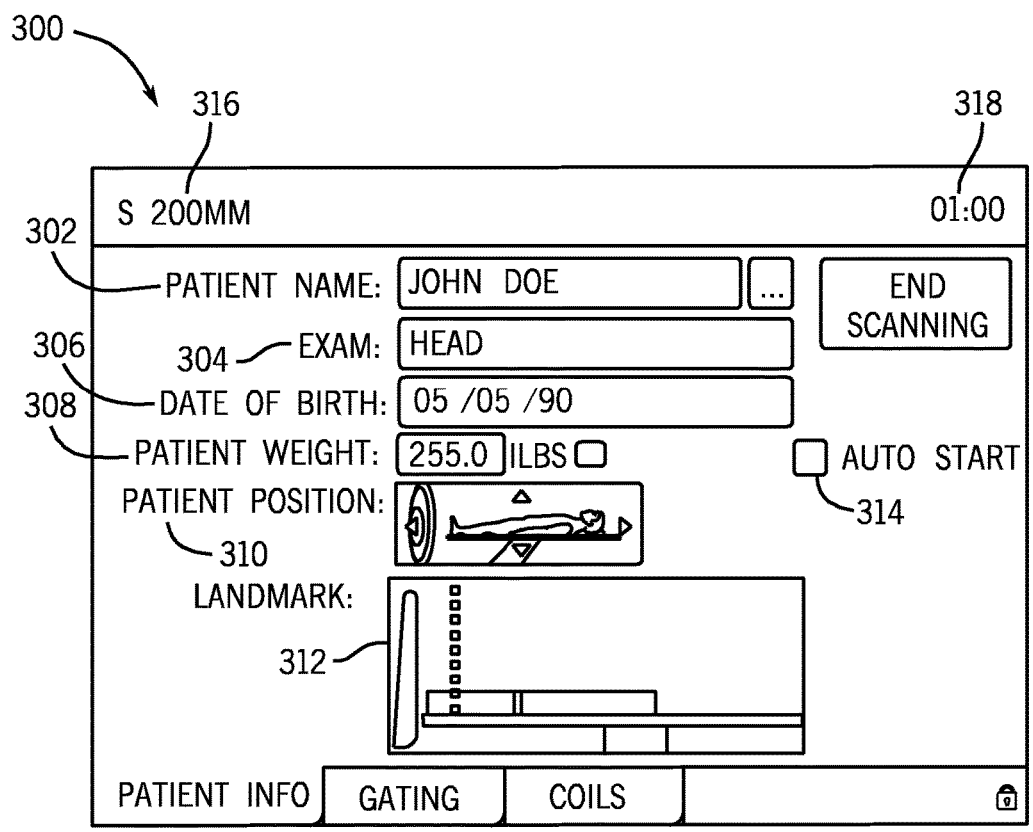
FIG. 3 shows an exemplary graphical user interface for receiving and displaying patient and scan information in accordance with an embodiment;.

FIG. 3 shows an exemplary graphical user interface for receiving and displaying patient and scan information in accordance with an embodiment. The graphical user interface 300 includes fields for a patient name 302, an exam or clinical indication 304, a date of birth 306, and a patient weight 308. The graphical user interface 300 also displays a patient position 310, a table position 316 and a scan time 318. In one embodiment, a graphical user interface may be provided that includes a list of patients. Accordingly, a user may select the next patient to be scanned from the list of patients provided on the display in the scan room. The list of patients may include, for example, a list of patient identifiers (e.g., name or identification number) or a list of patient identifiers and an associated protocol for each patient. In another embodiment, the patient list provided on the display may include an "emergency patient" option that can be used for an emergency scan. If an emergency scan of a patient is needed, the operator may select the option "emergency patient" from the patient list, select or enter a protocol and input the minimal necessary patient information (e.g., weight) using the graphical user interface on the display and the input device in the scan room. In an alternative embodiment, a number of emergency patient options may be provided in the patient list, with each associated with a particular protocol. For example, the patient list may include options for "emergency—brain," "emergency—knee," etc.

Display 82 (shown in FIG. 1) and input device 84 (shown in FIG. 1) in the scan room 80 (shown in FIG. 1) may also be used to access and view operator instructions relating to the operation of the MRI system or to the specific MRI exam being conducted. The operator instructions may be stored in a memory of, for example, the computer system 20 (shown in FIG. 1) or system control 32 (shown in FIG. 1) of the MRI system. The display and input device in the scan room may be used to request and receive the operator instructions from the computer system or system control.

The display and input device in the scan room can be used to control an automatic start mode that enables a scan to be initiated automatically based on the detection of an event. The automatic start mode (or auto start) for a scan may be selected and configured using the input device and display in the scan room. When the automatic start feature is enabled, the scan starts automatically when the MRI system detects a predefined event, such as an event that indicates when an operator is at a predetermined location, for example, when the operator leaves the scan room. A control in the scan room, such as a hard key, switch or button on the input device or a button or menu item on the display may be used to control and configure (e.g., select a time delay) the automatic start mode. For example, in one embodiment as shown in FIG. 3, an automatic start mode check box 314 in the graphical user interface 300 may be utilized to enable or disable the automatic start feature.

Returning to FIG. 2, at block 206 the operator performs the set up of the patient and scan within the scan room to configure the patient and the imaging assembly equipment for the MRI exam. The display 82 (shown in FIG. 1) and input device 84 (shown in FIG. 1) are configured to allow the operator to perform, control and verify the patient and scan set up for the MRI exam. In one embodiment, the display and input device may be used to verify whether cardiac leads or respiratory bellows have been correctly configured and correctly placed on the patient or subject. The display and input device may also be used to control a patient comfort system such as patient airflow within the magnet bore, lighting, audio, video, etc. Controls may also be provided for the patient table position, e.g., up/down, in/out and, as shown in FIG. 3, the patient position 310 may be displayed on the scan room display. As mentioned above, the display and input device may be used to access and view operator instructions relating to the operation of the MRI system or to the specific MRI exam being conducted.

Figure 4:
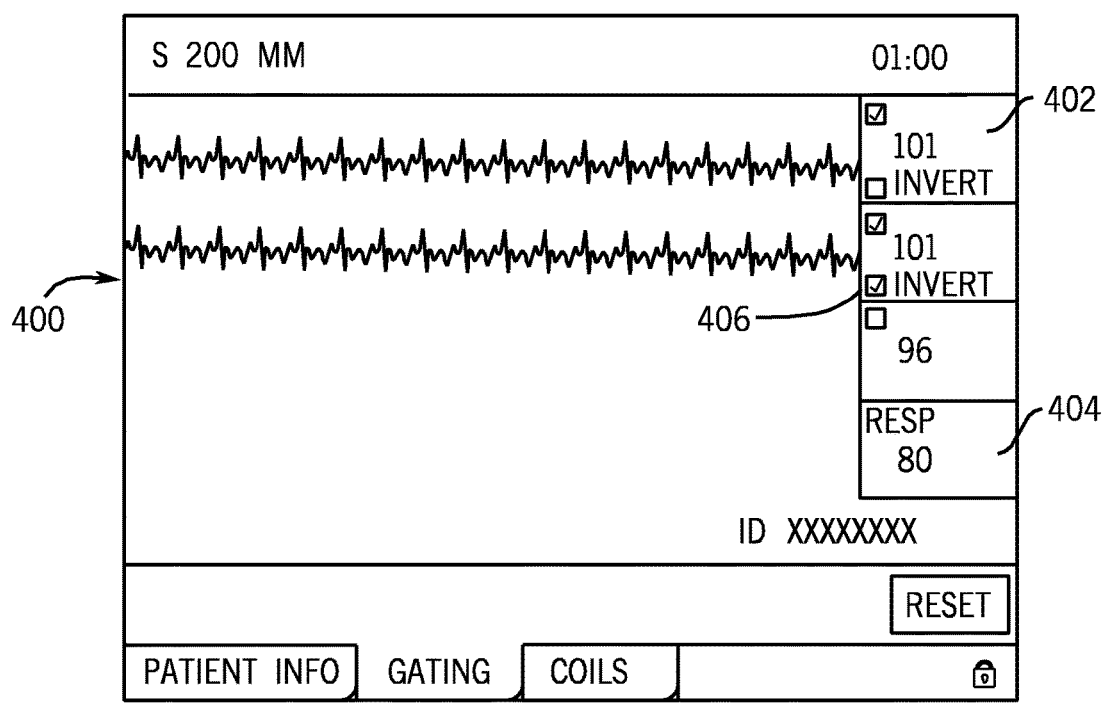
FIG. 4 shows an exemplary graphical user interface for receiving and displaying gating controls in accordance with an embodiment.

In another embodiment, the display and input device may be configured to receive and display gating control information including, but not limited to, trigger select, waveform invert, wireless connection status, waveform and gating selection (e.g., independent vector gating, standard gating, ECG noise filter, third party patient monitoring with gating, respiratory, PG display), cardiac sweep rate, synchronization of cardiac and respiratory sweep rates, trigger lead, and cardiac trigger level. FIG. 4 shows an exemplary graphical user interface for receiving and displaying gating controls in accordance with an embodiment. Graphical user interface 400 includes a cardiac waveforms display 402, a respiratory waveforms display 404, wireless connection status and enables control of the trigger select and waveform invert 406 options.

Figure 5:
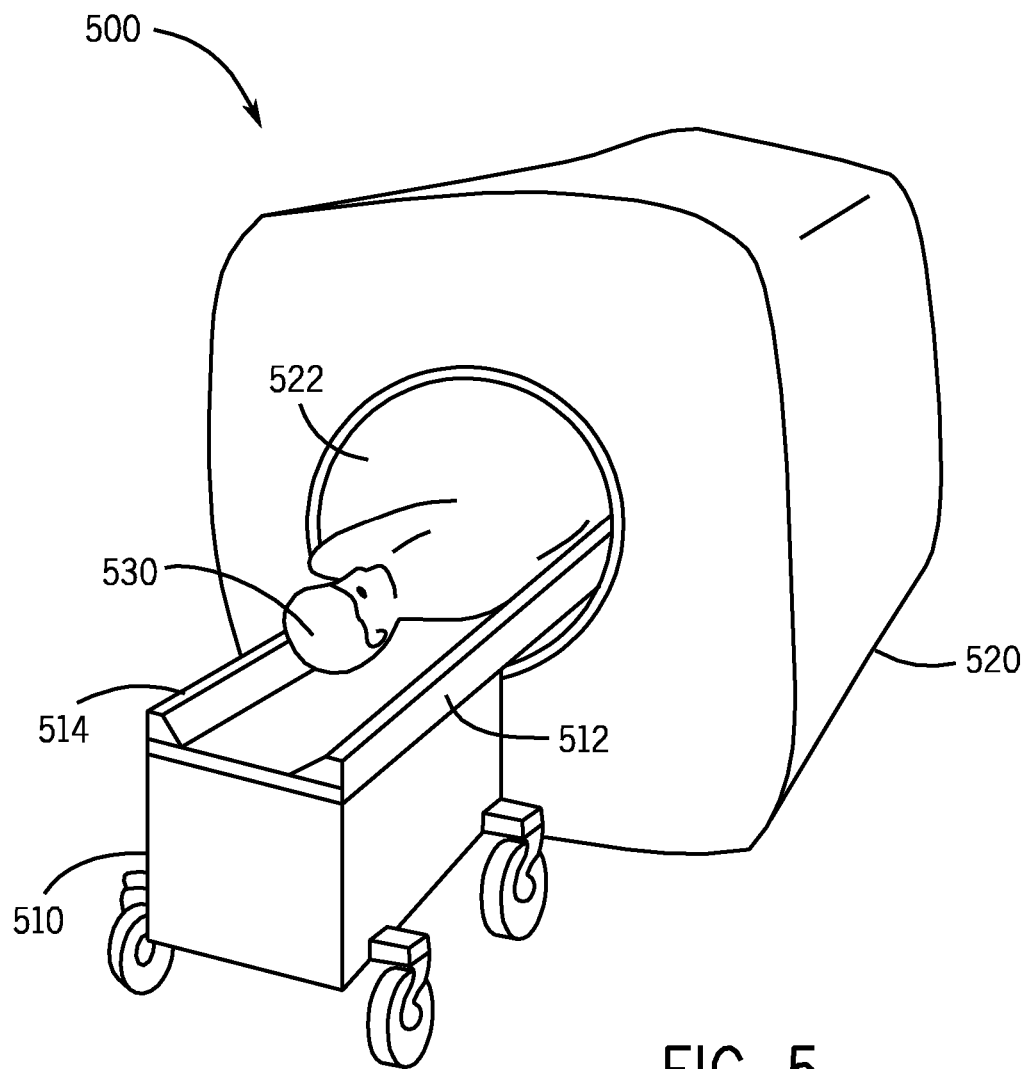
FIG. 5 is a schematic diagram showing an exemplary cylindrical magnetic resonance imaging system including a landmarking module in accordance with an embodiment.

Returning to FIG. 2, the patient and scan set up may also include the selection of landmarks for the scan. The MRI system 10 (shown in FIG. 1) may include a landmarking module that allows an operator to mark the location of an anatomical landmark. In one embodiment, the landmarking module is a pressure sensitive strip. FIG. 5 is a schematic diagram showing an exemplary cylindrical magnetic resonance imaging system including a landmarking module in accordance with an embodiment. In FIG. 5, the MRI system 500 includes a magnet 520 and a mobile patient transport table 510. Magnet 520 (equipped with RF and gradient coils) has a bore 522 having a useful diameter sufficient to accommodate a patient 530 shown in a supine position supported by a patient cradle 512. A pressure sensitive strip 514 is located along the edge of the patient cradle 512. The pressure sensitive strip 514 sends a signal (e.g., a digital signal) that indicates the location of an applied pressure. The display 82 (shown in FIG. 1) in the scan room 80 (shown in FIG. 1) is configured to display the selected landmark location relative to the patient table and/or relative to an RF coil or coils to ensure accuracy. Referring to FIG. 3, the exemplary graphical user interface 300 includes a landmark display 312 showing the position of the selected landmark. In other embodiments, a landmark may be identified using other known landmarking modules such as a laser guidance system. An operator may also provide landmark information using the display and input device in the scan room. In another embodiment, the anatomical landmarks may automatically be identified by the MRI system using methods known in the art and displayed on the display in the scan room. When fixed RF coils are used where the operator does not need to specify a landmark location, a default landmark can be shown on the scan room display.

Figure 6:
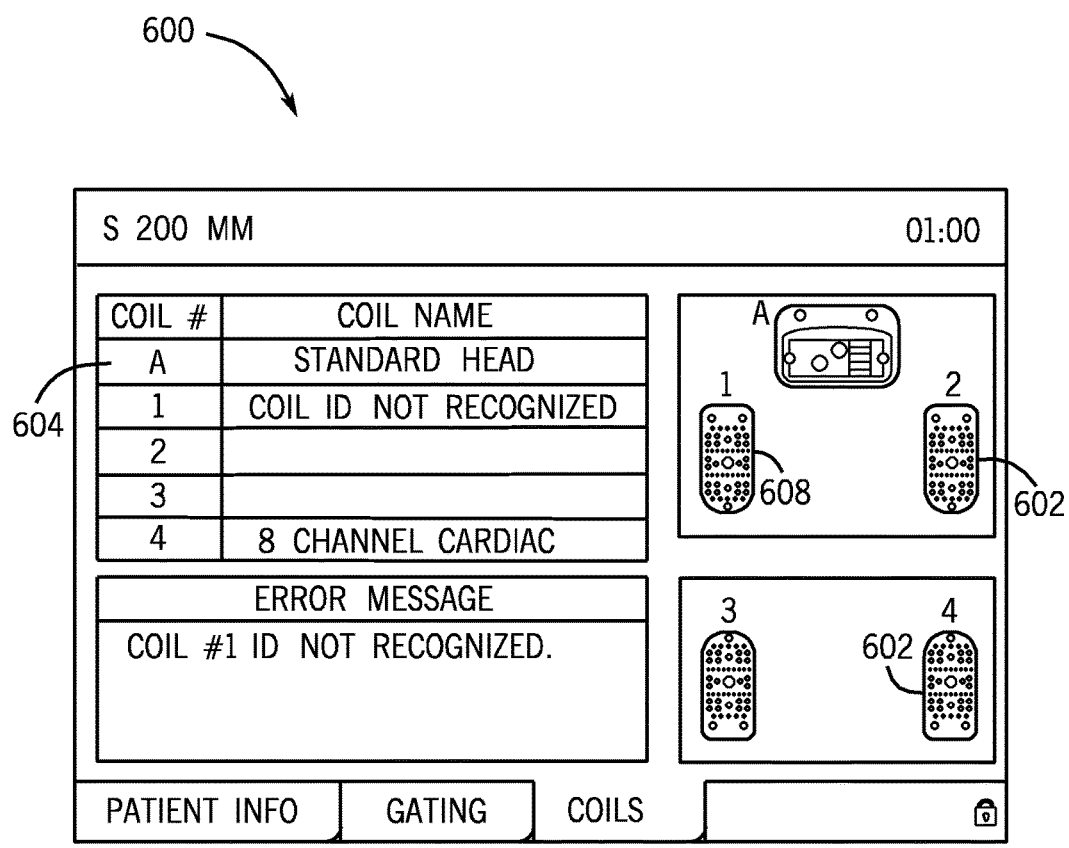
FIG. 6 shows an exemplary graphical user interface for coil connections and status in accordance with an embodiment.

Returning to FIG. 2, the patient and scan setup may also involve the selection of RF coils for the scan. The RF coils may be selected by the operator or may be selected automatically by the MRI system based on the scan prescription. The display 82 (shown in FIG. 1) and the input device 74 (shown in FIG. 1) in the scan room 80 (shown in FIG. 1) are configured to allow an operator to select RF coils for the scan. The selection of RF coils elements is typically based on the desired scanning volumes(s). For example, if a scanning volume encompassing the knee is defined, all of the RF coils elements that comprise a knee phased array coil may be selected for activation during the scanning. If multiple volumes have been defined, then multiple sets of RF coils may be selected that are appropriate for each scanning volume. For an automatic selection, the MRI system may detect which RF coil elements are available for activation and select the appropriate coil elements from the available RF coil elements. The display and input device in the scan room may also be used to enter and view the position of a "floating" RF coil or coils. A position or location of a "floating" coil may also be indicated using a pressure sensitive strip (as described above with respect to FIG. 5) and displayed on the display in the scan room. Once an appropriate RF coil or coils are selected (either by the operator or automatically by the MRI system), the selected RF coils and their positions may be shown on the display in the scan room. The operator may use the display and input device in the scan room to verify the RF coil connections and compatibility (e.g., whether the coils are connected properly, whether the coils are compatible with the scan, etc.). FIG. 6 shows an exemplary graphical user interface showing coil connections and status in accordance with an embodiment. The graphical user interface 600 shows a listing 604 of coils as well as a display 602 showing the RF coil connectors and the status of the RF connections (e.g., a selected coil connection 608 may be highlighted). Returning to FIG. 2, the display and input device in the scan room may also be used to provide the MR system with other positional information. For example, for a full body scan, the position of the patient's head and feet may be provided using the display and input device in the scan room.

Referring again to FIG. 2, once the patient and scan set up is complete, the operator may advance to scan at block 208. The operator may use, for example, the input device in the scan room or a switch or button on the imaging assembly 52 (shown in FIG. 1) to select to advance to scan. When the operator selects advance to scan, the patient table 86 (shown in FIG. 1) moves to an appropriate position within the magnet assembly for the scan. As mentioned above with respect to FIG. 3, the scan room display may be used to view the patient position. At block 210, the scan is started. In one embodiment, a control in the scan room, such as a hard key, switch or button on the input device or a button or menu item on the display, may be used to start a scan. Alternatively, as discussed above, an automatic start mode may be selected and configured (e.g., by using the input device and display in the scan room) to automatically start a scan based on a predefined event.

During the scan, the operator may monitor and control scan operations using the display 82 (shown in FIG. 1) and input device 84 (shown in FIG. 1) in the scan room 80 (shown in FIG. 1) at block 212. In an embodiment, a timer may be displayed on the display 82 to indicate the time remaining for various time periods during the scan (for example, a predetermined time period after a contrast agent has been injected). In addition, the status of various series/scans for an exam or protocol may also be displayed on the display 82 in the scan room. Various MRI procedures require an operator (e.g., a physician) to review and/or manipulate images, such as MR guided biopsy, MR guided brachytherapy, other MR interventional procedures and stress studies (e.g., cardiac stress studies). The display and/or input device in the scan room may include controls that allow an operator to view images, select images and manipulate images (e.g., window/level, RAS coordinates of a cursor, pan, zoom, flip, rotate, scroll, etc.). The display and input device in the scan room allow procedures that require image review and/or manipulation to be done more efficiently. For example, for a cardiac stress study, the stress MRI images can be evaluated with the patient and physician in the scan room simultaneously and from within the scan room an operator can terminate the stress study faster and therefore reduce the time for which the patient is kept under stress. In addition, during a scan the display and input device may be used to access and view operator instructions, stop a scan or pause a scan.

If the scan is complete at block 214, the exam is stopped at block 216. An operator may then select the next patient to scan. If the scan is not complete at block 214, the operator may continue to monitor and control the scan operations in the scan room at block 212.

As mentioned previously, in another embodiment, the display 82 (shown in FIG. 1) and input device 84 (shown in FIG. 1) located in the scan room also facilitate an "emergency" scan of a patient. An operator is able to set up a patient in the imaging assembly (i.e., on the patient table) and using the display and/or input device in the scan room enter the minimal necessary patient information (e.g., a patient weight), select a scan protocol and start a scan.

In yet another embodiment, the display and input device in the scan room are configured to allow a field engineer to access and view service procedure instructions regarding how to perform service procedures. The service procedure instructions may be stored in a memory of, for example, the computer system 20 (shown in FIG. 1) or system control 32 (shown in FIG. 1) of the MRI system. The display and input device in the scan room may be used to request and receive the service procedure instructions from the computer system or system control. In addition, the test results generated by the service procedures performed may be shown on the display in the scan room. Accordingly, the efficiency of the field engineer may be improved.

Computer-executable instructions for performing and configuring a magnetic resonance imaging exam according to the above-described method may be stored on a form of computer readable media. Computer readable media includes volatile and nonvolatile, removable and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital versatile disks (DVD) or other optical storage, magnetic cassettes, magnetic tape, magnetic disk storage or other magnetic storage devices, or any other medium which can be used to store the desired instructions and which may be accessed by MRI system 10 (shown in FIG. 1), including by internet or other computer network forms of access.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims. The order and sequence of any process or method steps may be varied or re-sequenced according to alternative embodiments.

Many other changes and modifications may be made to the present invention without departing from the spirit thereof. The scope of these and other changes will become apparent from the appended claims.

We claim:

1. A method for configuring and controlling a magnetic resonance imaging (MRI) exam, the method comprising:
    receiving, at a computer disposed in a control room, information including patient information and scan information regarding an initial set up of a patient for a scan for the MRI exam from a user using a display and an input device in a scan room of a magnetic resonance imaging system, the input device forming part of the display, the input device and display shielded within the scan room;
    controlling, with the computer disposed in the control room, MRI scanner operations in the scan room using operator input received during performance of the scan via the input device at an imaging assembly performing the scan for the MRI exam; and
    displaying a set of patient and scan data on the display in the scan room based on the received information.

2. A method according to claim 1, further comprising:
    receiving, from the user, a verification of the set of patient and scan data using the display and input device in the scan room.

3. A method according to claim 1, wherein the information received by the computer disposed in the control room includes patient identification information.

4. A method according to claim 1, wherein the information received by the computer disposed in the control room includes a location of an anatomical landmark.

5. A method according to claim 1, wherein the displayed set of patient and scan data includes a location of an anatomical landmark.

6. A method according to claim 1, wherein the information received by the computer disposed in the control room includes a selection of at least one RF coil.

7. A method according to claim 6, wherein the information received by the computer disposed in the control room includes a location of the at least one RF coil.

8. A method according to claim 6, wherein the displayed set of patient and scan data includes a location of the at least one RF coil.

9. A method according to claim 1, wherein the information received by the computer disposed in the control room includes positional information regarding the patient.

10. A method according to claim 1, wherein the information received by the computer disposed in the control room includes gating control information.

11. A method according to claim 1, wherein the information received by the computer disposed in the control room includes settings for a patient comfort system.

12. A method according to claim 1, further comprising monitoring the MRI scanner operations in the scan room using the display during performance of the scan.

13. A method according to claim 1, further comprising reviewing, in the scan room using the display, an image, and controlling the scanning operations using the input device based on the reviewed image.

14. A magnetic resonance imaging (MRI) system comprising:
    an imaging assembly located in a scan room;
    a controller coupled to the imaging assembly and located in a separate control room;
    a display coupled to the controller and located in the scan room, the display configured to display at least one graphical user interface relating to an initial set up of a patient and a scan for a magnetic resonance imaging (MRI) exam; and
    an input device forming part of the display and coupled to the controller, the input device and display shielded within the scan room, the input device located in the scan room at the imaging assembly and configured to receive patient information and scan information regarding the initial set up of a patient for a scan for the MRI exam, the controller configured to control scan operations of the imaging assembly using control input received from an operator in the scan room via the input device during performance of the scan.

15. A magnetic resonance imaging system according to claim 14, wherein the at least one graphical user interface is configured to display a location of an anatomical landmark.

16. A magnetic resonance imaging system according to claim 14, wherein the at least one graphical user interface is configured to display a location of at least one RF coil.

17. A magnetic resonance imaging system according to claim 14, wherein the at least one graphical user interface is configured to display positional information regarding the patient.

18. A magnetic resonance imaging system according to claim 14, wherein the at least one graphical user interface is configured to display gating control information.

19. A magnetic resonance imaging system according to claim 14, wherein the at least one graphical user interface is configured to display settings for a patient comfort system.

20. A magnetic resonance imaging system according to claim 14, wherein the at least one graphical user interface is configured to display a list of patients.

21. A magnetic resonance imaging system according to claim 20, wherein the list of patients includes an emergency patient option.

22. A magnetic resonance imaging system according to claim 14, wherein the display is configured to receive control signals from the controller and the input device.

23. A magnetic resonance imaging system according to claim 14, wherein the input device is configured to receive a request for a set of operator instructions regarding a function of the MRI system and the graphical user interface is configured to display the set of operator instructions.

24. A method for configuring and controlling a magnetic resonance imaging (MRI) exam, the method comprising:
    receiving, at a computer disposed in a control room, initial information for the MRI exam from a user via a display and input device in a scan room, the display and input device shielded within the scan room and forming part of an imaging assembly, the initial information including patient information and scan information;

receiving additional information after a patient is set-up within the imaging assembly, the additional information completing a patient and scan set-up, the initial information and the additional information received by the computer from the operator within the scan room via the display and input device;

displaying a set of patient and scan data on the display in the scan room based on the received initial information and additional information;

receiving, via the input device, a user input to start a scan of the patient, the operator not leaving the scan room from when the initial information is received and the additional information is received to when the user input starting the scan is received; and controlling, with the computer disposed in the control room, MRI scanner operations of the imaging assembly based on the received initial information, the additional information, and control information received from the operator in the scan room at the display and input device during the performance of the scan.

* * * * *